United States Patent [19]

Sheridan et al.

[11] Patent Number: 5,747,244

[45] Date of Patent: May 5, 1998

[54] NUCLEIC ACID PROBES IMMOBILIZED ON POLYSTYRENE SURFACES

[75] Inventors: Patrick Sheridan, San Leandro; Chu-An Chang, Piedmont; Joyce Running, Concord; Michael S. Urdea, Alamo, all of Calif.

[73] Assignee: Chiron Corporation, Emeryville, Calif.

[21] Appl. No.: 813,338

[22] Filed: Dec. 23, 1991

[51] Int. Cl.$^6$ .............................. C12Q 1/68; C07H 21/04; C07K 17/08; C08L 89/00

[52] U.S. Cl. .............................. 435/6; 435/91.2; 536/24.3; 530/350; 106/124

[58] Field of Search .............................. 530/810, 812, 530/815, 350; 435/6, 174, 177, 180, 181, 7.92; 106/124; 536/24.3

[56] References Cited

U.S. PATENT DOCUMENTS

| | | | |
|---|---|---|---|
| 4,657,853 | 4/1987 | Freytag et al. | 435/7.92 |
| 4,657,873 | 4/1987 | Gadow et al. | 435/7.9 |
| 4,868,105 | 9/1989 | Urdea et al. | 435/6 |

OTHER PUBLICATIONS

U.S. Patent Application Serial No. 07/558,897 (filed 27 Jul. 1990).

Maniatis et al., "Molecular Cloning a Laboratory Manual", Cold Spring Harbor Laboratory, New York, 1982, pp. 314–315.

Owen et al., J. Clin. Microbiol. 27 (10): 2338–2343 (Oct. 1989).

*Primary Examiner*—Stephanie W. Zitomer
*Attorney, Agent, or Firm*—Tyler Dylan; Kenneth M. Goldman; Robert P. Blackburn

[57] ABSTRACT

Nucleic acid probes are immobilized on polystyrene surfaces such as the wells of microtiter plates for use in solution phase nucleic acid sandwich hybridization assays, particularly those using large branched DNA amplification multimers, by: (a) cleansing the surface by washing it sequentially with a strong acid, a strong base, and water, (b) passively adsorbing a polypeptide having primary amino groups onto the cleansed surface, and (c) covalently bonding the probe to the adsorbed polypeptide via a base-stable bifunctional crosslinking agent, and (d) subjecting the surface to conditions that simulate the hybridization conditions used in the assay.

6 Claims, 6 Drawing Sheets

:27A
YGAAGCGGGCACAGTCARRCAAGARAGCAGGGC  (nt879=C)

:28A
RTARAGCCCYGWGGAGTTGCGCACTTGGTRGGC

:29A
RATACTCGAGTTAGGGCAATCATTGGTGACRTG

:30A
AGYRTGCAGGATGGYATCRKBCGYCTCGTACAC

:31A
GTTRCCCTCRCGAACGCAAGGGACRCACCCCGG

:32A
CGTRGGGGTYAYCGCCACCCAACACCTCGAGRC

:33A
CGTYGYGGGGAGTTTGCCRTCCCTGGTGGCYAC

:34A
CCCGACAAGCAGATCGATGTGACGTCGAAGCTG

:35A
CCCCACGTAGARGGCCGARCAGAGRGTGGCGCY

:36A
YTGRCCGACAAGAAAGACAGACCCGCAYARGTC

:37A
CGTCCAGTGGYGCCTGGGAGAGAAGGTGAACAG

:38A
GCCGGGATAGATRGARCAATTGCARYCTTGCGT

:39A
CATATCCCATGCCATGCGGTGACCCGTTAYATG

:40A
YACCAAYGCCGTCGTAGGGGACCARTTCATCAT

:41A
GATGGCTTGTGGGATCCGGAGYASCTGAGCYAY

:42A
GACTCCCCAGTGRGCWCCAGCGATCATRTCCAW

:43A
CCCCACCATGGAGAAATACGCTATGCCCGCYAG

:44A
TAGYAGCAGYACTACYARGACCTTCGCCCAGTT

:45A
GSTGACGTGRGTKTCYGCGTCRACGCCGGCRAA
(nt1505=G)

FIG. 2A

:27B
GGAAGYTGGGATGGTYARRCARGASAGCARAGC  (nt879=C)

:28B
GTAYAYYCCGGACRCGTTGCGCACTTCRTAAGC

:29B
AATRCTTGMGTTGGAGCARTCGTTYGTGACATG

:30B
RGYRTGCATGATCAYGTCCGYYGCCTCATACAC

:31B
RTTGTYYTCCCGRACGCARGGCACGCACCCRGG

:32B
CGTGGGRGTSAGCGCYACCCAGCARCGGGAGSW

:33B
YGTRGTGGGGAYGCTGKHRTTCCTGGCCGCVAR

:34B
CCCRACGAGCAARTCGACRTGRCGTCGTAWTGT

:35B
YCCCACGTACATAGCSGAMSAGARRGYAGCCGY

:36B
CTGGGAGAYRAGRAAAACAGATCCGCARAGRTC

:37B
YGTCTCRTGCCGGCGAGSBGAGAAGGTGAAYAG

:38B
GCCGGGATAGAKKGAGCARTTGCAKTCCTGYAC

:39B
CATATCCCAAGCCATRCGRTGGCCTGAYACGTG

:40B
CACTARGGCTGYYGTRGGYGACCAGTTCATCAT

:41B
GACRGCTTGTGGGATCCGGAGTAACTGCGAYAC

:42B
GACTCCCCAGTGRGCCCCCGCCACCATRTCCAT

:43B
SCCCACCATGGAWWAGTAGGCAAGGCCCGCYAG

:44B
GAGTAGCATCACAATCAADACCTTAGCCCAGTT

:45B
YGWCRYGYRGGTRTKCCCGTCAACGCCGGCAAA
(nt1505=Y)

FIG. 2B

:HCV.33.1
TCCTCACAGGGGAGTGATTCATGGTGGAGTGTC

:HCV.33.2
ATGGCTAGACGCTTTCTGCGTGAAGACAGTAGT

:HCV.33.3
GCCTGGAGGCTGCACGRCACTCATACTAACGCC

:HCV.33.4
CGCAGACCACTATGGCTCTYCCGGGAGGGGGGG

:HCV.33.5
TCRTCCYGGCAATTCCGGTGTACTCACCGGTTC

:HCV.33.6
GCATTGAGCGGGTTDATCCAAGAAAGGACCCGG

:HCV.33.7
AGCAGTCTYGCGGGGGCACGCCCAARTCTCCAG

:HCV.33.8
ACAAGGCCTTTCGCGACCCAACACTACTCGGCT

:HCV.33.9
GGGGCACTCGCAAGCACCCTATCAGGCAGTACC

:HCV.33.10
YGTGCTCATGRTGCACGGTCTACGAGACCTCCC

:HCV.33.11
GTTACGTTTGKTTYTTYTTTGRGGTTTRGGAWT

:HCV.33.12
CGGGAACTTRACGTCCTGTGGGCGRCGGTTGGT

:HCV.33.13
CARGTAAACTCCACCRACGATCTGRCCRCCRCC

:HCV.33.14
RCGCACACCCAAYCTRGGGCCCCTGCGCGGCAA

:HCV.33.15
AGGTTGCGACCGCTCGGAAGTCTTYCTRGTCGC

FIG. 3A

:HCV.33.16A
RCGHRCCTTGGGGATAGGCTGACGTCWACCTCG

:HCV.33.16B
RCGHRCCTTGGGGATAGGTTGTCGCCWTCCACG

:HCV.33.17
YCCRGGCTGRGCCCAGRYCCTRCCCTCGGRYYG

:HCV.33.18
BSHRCCCTCRTTRCCRTAGAGGGGCCADGGRTA

:HCV.33.19
GCCRCGGGGWGACAGGAGCCATCCYGCCCACCC

:HCV.33.20
CCGGGGGTCYGTGGGGCCCCAYCTAGGCCGRGA

:HCV.33.21
ATCGATGACCTTACCCAARTTRCGCGACCTRCG

:HCF.33.22
CCCCATGAGRTCGGCGAAGCCGCAYGTRAGGGT

:HCV.33.23
GCCYCCWARRGGGGCGCCGACGAGCGGWATRTA

:HCV.33.24
AACCCGGACRCCRTGYGCCARGGCCCTGGCAGC

:HCV.33.25
RTTCCCTGTTGCATAGTTCACGCCGTCYTCCAG

:HCV.33.26
CARRAGGAAGAKAGAGAAAGAGCAACCRGGMAR

FIG. 3B

NUCLEIC ACID PROBES IMMOBILIZED ON POLYSTYRENE SURFACES

TECHNICAL FIELD

This invention is in the field of nucleic acid hybridization assays. More specifically, it relates to an improved method for immobilizing nucleic acid probes on polystyrene surfaces for the purpose of removing analyte nucleic acid from solution.

BACKGROUND ART

Commonly owned U.S. Pat. No. 4,868,105 describes a solution phase nucleic acid sandwich hybridization assay in which analyte nucleic acid is first hybridized in solution to a labeling probe set and to a capturing probe set in a first vessel. The probe-analyte complex is then transferred to a second vessel that contains a solid-phase-immobilized probe that is complementary to a segment of the capturing probes. The segments hybridize to the immobilized probe, thus removing the complex from solution. Having the analyte in the form of an immobilized complex facilitates subsequent separation steps in the assay. Ultimately, single stranded segments of the labeling probe set are hybridized to labeled probes, thus permitting the analyte-containing complex to be detected via a signal generated directly or indirectly from the label.

Commonly owned European Patent Application Pub. No. 317,077 discloses a variation in the assay described in U.S. Pat. No. 4,868,105 in which the signal generated by the labeled probes is amplified. The amplification involves the use of nucleic acid multimers. These multimers are branched polynucleotides that are constructed to have a segment that hybridizes specifically to the analyte nucleic acid or to a nucleic acid (branched or linear) that is bound to the analyte and iterations of a second segment that hybridize specifically to the labeled probe. In the assay employing the multimer, the initial steps of hybridizing the analyte to label or amplifier probe sets and capturing probe sets in a first vessel and transferring the complex to another vessel containing immobilized nucleic acid that will hybridize to a segment of the capturing probes are followed. The multimer is then hybridized to the immobilized complex and the labeled probes in turn hybridized to the second segment iterations on the multimer. Since the multimers provide a large number of sites for label probe attachment, the signal is amplified.

Commonly owned copending European Patent Application Pub. No. 541,693, describes the preparation of large comb-type branched polynucleotide multimers for use in the above-described solution phase assay. The combs provide greater signal enhancement in the assays than the smaller multimers.

As described in EP 317,077, two types of solution phase nucleic acid sandwich hybridization assay formats are employed: a bead assay procedure, and a microtiter dish assay procedure. In practice, the microtiter dish assay is preferred. The procedure for immobilizing the capture probe in the wells of polystyrene microtiter dishes was as follows. Poly-(phenylalanyl-lysine) was passively adsorbed onto the surfaces of the wells of the dish. The oligonucleotide to be immobilized was synthesized by solid state procedures to have a 5' modified cytidine (the $N^4$-(6-aminocaproyl-2-aminoethyl derivative of cytidine). This oligonucleotide was activated by reacting the modified cytidine with the bifunctional crosslinking agent ethylene glycol bis(succinimydyl succinate) and the activated oligonucleotide was added to the wells and incubated at room temperature. During the incubation, the other functional group of the crosslinking agent reacts with the primary amino groups of the adsorbed poly-(phenylalanyl-lysine) to thus immobilize the oligonucleotide. The wells were then washed with phosphate-buffered saline (PBS), coated with HM buffer (0.1% SDS, 4×SSC, 1 mg/ml sonicated salmon sperm DNA, 1 mg/ml poly-A, 10 mg/ml bovine serum albumin), washed again with PBS, and stored for use. As indicated, the initial hybridization of the analyte to the capturing and amplifying probe sets was carried out in separate wells under basic conditions. Following the hybridization, the solution was neutralized and the neutralized solution transferred to the wells containing the immobilized probe. The initial hybridization could not be carried out in the wells containing the immobilized capture probe because the immobilized complex was unstable under the hybridization conditions.

The present invention provides several advantages over the above-described prior procedure. First, it permits the entire assay, including the initial hybridization, to be carried out in one well. Second, it improves the reproduceability of the assay. Finally, in its preferred embodiment employing large comb-type multimers, it provides reduced background signal.

DISCLOSURE OF THE INVENTION

One aspect of the present invention is a process for immobilizing a nucleic acid probe having a first functional group on a polystyrene surface for use in a solution phase nucleic acid sandwich hybridization assay comprising:

(a) cleansing the polystyrene surface by washing it sequentially with a strong acid, a strong base and water;

(b) passively adsorbing a polymer having a second functional group(s) onto the polystyrene surface; and (c) covalently bonding the nucleic acid probe to the adsorbed polymer via a base-stable linkage.

Another aspect of the invention is an article of manufacture for use in a solution phase nucleic acid sandwich hybridization assay comprising a polystyrene surface having a polymer adsorbed thereon and a nucleic acid probe covalently bonded to the polymer via a base-stable linkage.

Still another aspect of the invention is an improvement in a solution phase nucleic acid sandwich hybridization assay for detecting the presence of an analyte single-stranded nucleic acid in a sample wherein the assay comprises the steps of:

(a) contacting the sample under hybridizing conditions with a set of labeling probes each of which has a first segment that is complementary to the analyte and a second segment that is complementary to a segment of a DNA multimer and a set of capture probes each of which has a first segment that is complementary to the analyte and a second segment that is complementary to an oligonucleotide immobilized on a polystyrene surface;

(b) contacting the product of step (a) under hybridizing conditions with said oligonucleotide immobilized on a polystyrene surface;

(c) contacting the product of step (b) under hybridization conditions with said multimer; and (d) contacting the product of step (c) under hybridization conditions with a labeled oligonucleotide that hybridizes to the multimer and the improvement is the use in step (b) of an oligonucleotide that is immobilized to the polystyrene surface via an adsorbed polymer to which the oligonucleotide is covalently bound via a base-stable linkage.

BRIEF DESCRIPTION OF THE DRAWINGS

In the drawings:

FIGS. 2A, 2B, 3A and 3B are listings of sequences of segments of the probes described in Example 4.

MODES FOR CARRYING OUT THE INVENTION

Definitions

Figure 1:
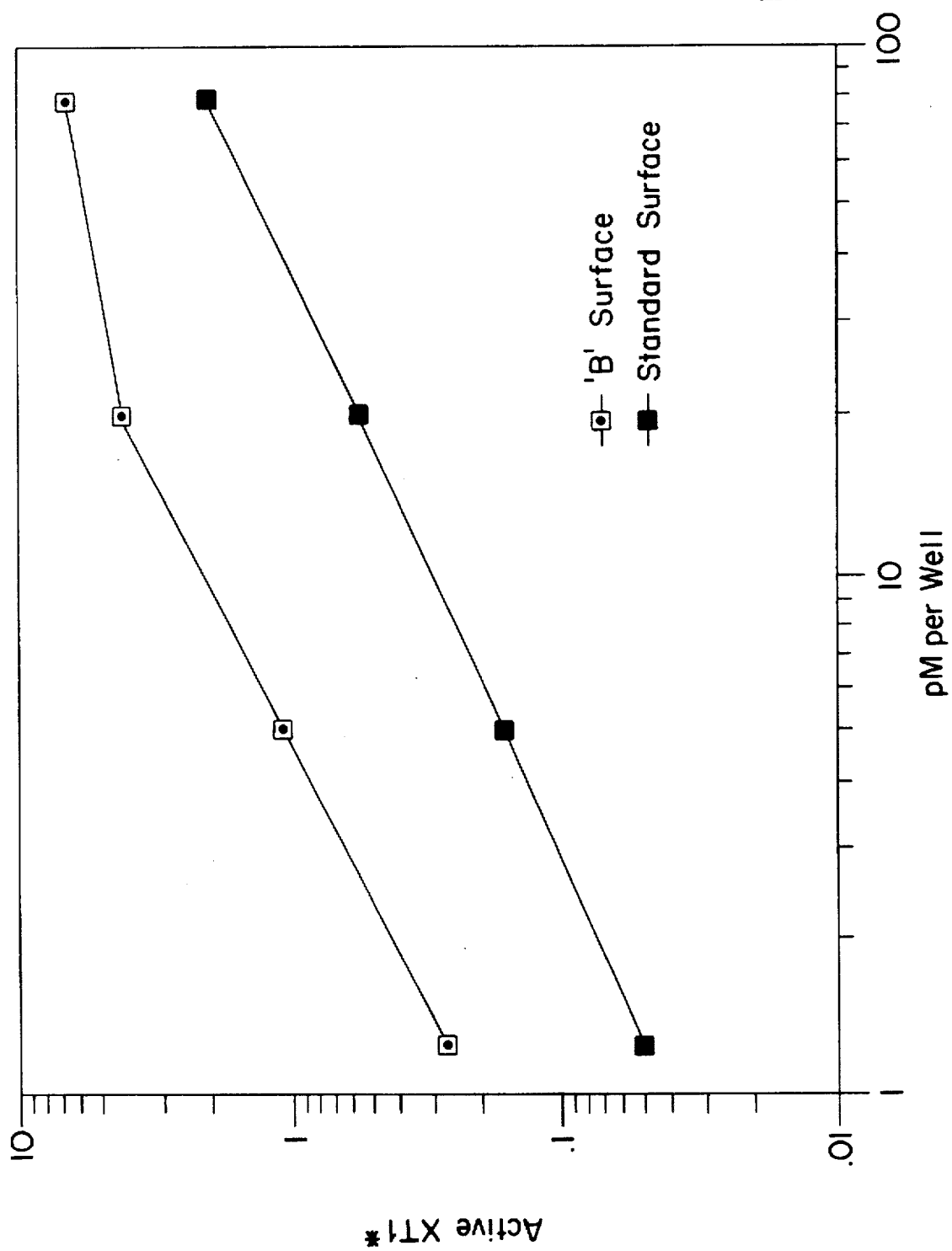
FIG. 1 is a graph of the results of the experiments described in Example 3.

The term "base-stable" as used to characterize the covalent linkages that are employed in this invention intends linkages that undergo no substantial degradation (e.g., breakage of covalent bonds due to hydrolysis) when contacted with 1 N NaOH at temperatures in the range of 4 to 70° C. or under conditions that are at least as stringent (e.g., simulate or are more stringent) as those used in the hybridization of the probes to the analyte in the solution-phase hybridization assay.

The term "bifunctional crosslinking agent" intends organic molecules that have two functional groups, one of which is capable of reacting with a functional group of the polymer employed in the invention to form a covalent bond between the agent and the polymer and the other of which is capable of reacting with a functional group on the nucleic acid probe that is to be immobilized to form a second covalent bond between the agent and the probe. The resulting ternary complex comprises the crosslinking agent bound covalently to both the polymer and the probe via reaction between the two functional groups of the agent and functional groups on the polymer and the probe. Preferably, the functional groups on the polymer and probe are primary amino groups and the functional groups on the agent are selected from those that react with primary amino groups (e.g., carboxyl, sulfonyl chloride or aldehyde groups).

"Solution phase nucleic acid hybridization assay" intends the assay techniques described and claimed in commonly owned U.S. Pat. No. 4,868,105 and EP 317,077.

A "modified nucleotide" intends a nucleotide monomer that may be stably incorporated into a polynucleotide and which has an additional functional group that will react with a functional group of the crosslinking agent.

A "multimer" intends a branched polynucleotide that is capable of hybridizing simultaneously directly or indirectly to analyte nucleic acid and to a multiplicity of labeled probes. The branching in the multimers is effected through covalent bonds and the multimers are composed of two types of oligonucleotide units that are capable of hybridizing, respectively, to analyte nucleic acid or nucleic acid hybridized to analyte nucleic acid and to a multiplicity of labeled probes. The composition and preparation of such multimers are described in EP 317,077 and EP 541,693, the disclosures of which are incorporated herein by reference.

Immobilization of Probe on Polystyrene Surface

While the following discussion is directed to immobilizing probes on the surfaces of the wells of conventional polystyrene microtiter plates, it will be appreciated that the invention methodology may be used to immobilize probes on other polystyrene surfaces employed in nucleic acid sandwich hybridizations, such as particles (beads), tubes, filters, columns, and the like.

The polystyrene surface is first cleansed by washing it successively with a strong acid, a strong base, and aqueous buffer. The acid will normally be a mineral acid such as hydrochloric, nitric, or sulfuric acid at a concentration of 0.1 to 5N. 1N hydrochloric acid is preferred. The surface will normally be contacted with the acid for 1 to 10 min at temperatures in the range of 4° to 37° C. The acid-treated wells are then washed with a neutral aqueous buffer such as phosphate-buffered saline. The strong base will normally be an alkali metal hydroxide (e.g., NaOH, KOH) at a concentration of 0.1 to 5N. 1N sodium hydroxide is preferred. Contact time between the surface and the base will usually be 1 to 10 min. The contact temperature will again typically be 4° to 37° C. Following the base treatment, the surface is again washed with neutral aqueous buffer.

The surface is coated with a polymer, preferably a polypeptide that has a multiplicity of reactive primary amino groups and which will passively adsorb onto polystyrene. The polypeptide will typically have an average of about 10% to 100% primary amine containing amino acid residues per molecule. The polypeptide may be a naturally occurring protein or a synthetic polypeptide. The synthetic polypeptide may be homopolymeric (composed of the same amino acid) or copolymeric (composed of two or more amino acids). Other reactive functionalities, such as sulfhydryl or carboxylates, on either natural or synthetic amino acids can be employed. Its molecular weight is not critical and will normally be in the range of 5,000 to 50,000 daltons. Examples of polypeptides that may be used in this capacity are polylysine, poly(phe-lys), poly(ala-glu), casein, and bovine serum albumin. Poly(phe-lys) (1:1 mol ratio of phe:lys) having a molecular weight in the range of 30,000 to 60,000 is preferred. The coating is carried out by contacting the cleansed polystyrene with a neutral (pH 6–8) aqueous buffer solution of the polypeptide. The concentration of polypeptide in the solution will normally be 0.1 to 10 mg/ml, more usually 0.5 to 1.5 mg/ml. The solution may optionally contain salt up to about 5M concentration. The polypeptide coating step will normally be carried out at 20° C. to 65° C. for 0.5 to 36 hr, preferably at 25° to 35° C. for 15 to 20 hr. Following this treatment, the surface is washed repeatedly with a neutral aqueous buffer to remove any unadsorbed polypeptide. Optionally, it may be subjected to conditions (pH, ionic strength, detergent, proteinases) that simulate or are more stringent than those used in the initial hybridization step of the assay to dislodge adsorbed polypeptide that would be susceptible to dislodgement during the initial hybridization.

The single-stranded oligonucleotide probe that is covalently bound to the adsorbed polypeptide may be prepared by the automated phosphoramidate method described by Warner et al., DNA (1984) 3:401, and purified according to Sanchez-Pescador and Urdea, DNA (1984) 3:339. They include a 5'-modified nucleotide or nonnucleotide linker that includes a functional group that provides a reactive site by which to couple the oligonucleotide to the crosslinking agent. A preferred modified nucleotide is the $N^4$-(6-aminocaproyl-2-aminoethyl) derivative of 5-methylcytidine. The preparation of that derivative is described in U.S. Pat. No. 4,868,105. Other modified nucleotides are described in U.S. Pat. No. 4,948,882. The length and base composition of the oligonucleotide probe will depend upon the length and base composition of the nucleic acid sequence to which it must hybridize. It will normally be 15 to 100 nucleotides in length, more usually 20 to 30 nucleotides in length. As described in EP 317,077 the 21 base oligonucleotide, 5'-XCACCACTTTCTCCAAAGAAG-3'. (SEQ ID NO: 1) where X represents the $N^4$-(6-aminocaproyl-2-aminoethyl) derivative of cytidine, has been chosen as a standard probe sequence.

The oligonucleotide is coupled to the base-stable bifunctional crosslinking agent via reaction between the functional group of the 5'-modified nucleotide of the oligonucleotide and one of the functional groups of the crosslinking agent. To avoid coupling oligonucleotide to both functional groups of the crosslinking agent, the agent is used in large excess (e.g., 50- to 1000-fold excess). A variety of crosslinking agents may be used as long as the functional criteria of base-stability and reactivity with the oligonucleotide and amino groups of the polypeptide are met. Examples of suitable crosslinking agents may be found in Pierce Chemical Catalog. The conditions of the coupling reaction will vary with the particular agent used. The crosslinking agent will normally be dissolved in a polar solvent and the solution added to a solution of the oligonucleotide in an aqueous buffer and the polar solvent. The coupling will normally be carried out at neutral (6–8) pH, and temperatures in the range of 4° C. to 25° C. for about 0.5 to 18 hr. The resulting oligonucleotide-crosslinking agent conjugate (sometimes referred to herein as "activated oligonucleotide") may be purified from unreacted starting materials and unwanted reaction products using conventional chromatographic procedures.

The polypeptide-coated surface is then contacted with a neutral aqueous buffered solution of the purified activated oligonucleotide under conditions that permit the remaining functional group of the crosslinking agent to react with an amino group of the adsorbed polypeptide. Typically this coupling reaction is carried out using excess activated oligonucleotide (10- to 100-fold excess is preferred) at 0° C. to 25° C. for 0.5 to 18 hr, preferably at 2° C. to 8° C. for 8 to 18 hr. After this reaction is complete, the surface is washed with an aqueous buffer to remove unreacted activated oligonucleotide from the surface. At this stage in the process, the surface is coated with adsorbed polypeptide to which the nucleic acid probe has been covalently bound via the crosslinking agent. In the case of standard microtiter wells, there will typically be 0.1 to 10 pmoles, preferably 0.4 to 0.7 pmoles, of immobilized nucleic acid probe per well.

When the surface is to be used in an amplified assay procedure, particularly an assay using the large comb-type multimers of EP 541,673, it is preferable to subject the surface to conditions that simulate the conditions (pH, ionic strength, temperature, detergent) that prevail during the solution phase hybridization step of the assay. Such treatment tends to dislodge any polypeptide-oligonucleotide complex that might be dislodged during the solution phase hybridization. Accordingly, in such instances the surface will be contacted with a mild basic solution containing a low concentration of a detergent (e.g., 0.1 to 0.5N NaOH containing 0.1 to 2.0 wt % sodium dodecyl sulfate (SDS)) at 25° to 65° C. for 10 to 180 minutes.) After this final treatment, the surface is aspirated. The surface is then washed with aqueous buffer. It may be stored in a humidity controlled environment at 0° C. to 10° C. pending use.

Use of Coated Polystyrene Surface In Solution Phase Hybridization Assay

The coated polystyrene surface is used in solution phase sandwich hybridizations as follows. In the instance where the coated surface is the inner surface of the well of a microtiter plate, the analyte nucleic acid is placed in the well with an excess of two single-stranded nucleic acid probe sets: (1) a set of capture probes, each having a first binding sequence complementary to the analyte and a second binding sequence that is complementary to nucleic acid bound to the well surface, and (2) a set of amplifier probes (branched or linear), each having a first binding sequence that is capable of specific binding to the analyte and a second binding sequence that is capable of specific binding to a segment of the multimer. By using an amplifier probe, the multimer may be designed to be a "universal" reagent and different multimers need not be made for each analyte. The resulting product is a three component nucleic acid complex of the two probes hybridized to the analyte by their first binding sequences. The second binding sequences of the probes remain as single-stranded segments as they are not complementary to the analyte. This complex hybridizes to the immobilized probe on the well surface via the second binding sequence. The resulting product comprises the complex bound to the well surface via the duplex formed by the oligonucleotide bound to the well surface and the second binding sequence of the capture probe. Unbound materials are then removed from the surface such as by washing.

The amplification multimer is then added to the bound complex under hybridization conditions to permit the multimer to hybridize to the available second binding sequence of the amplifier probe of the complex. The resulting complex is then separated from any unbound multimer by washing. The labeled oligonucleotide is then added under conditions which permit it to hybridize to the complementary oligonucleotide units of the multimer. The resulting immobilized labeled nucleic acid complex is then washed to remove unbound labeled oligonucleotide, and read.

The analyte nucleic acids may be from a variety of sources, e.g., biological fluids or solids, food stuffs, environmental materials, etc., and may be prepared for the hybridization analysis by a variety of means, e.g., proteinase K/SDS, chaotropic salts, etc. Also, it may be of advantage to decrease the average size of the analyte nucleic acids by enzymatic, physical or chemical means, e.g., restriction enzymes, sonication, chemical degradation (e.g., metal ions), etc. The fragments may be as small as 0.1 kb, usually being at least about 0.5 kb and may be 1 kb or higher. The analyte sequence is provided in single-stranded form for analysis. Where the sequence is naturally present in single-stranded form, denaturation may not be required. However, where the sequence is present in double-stranded form, the sequence will be denatured. Denaturation can be carried out by various techniques, such as alkali, generally from about 0.05 to 0.2M hydroxide, formamide, salts, heat, or combinations thereof.

The first binding sequences of the capture probe and amplifier probe that are complementary to the analyte sequence will each be of at least 15 nucleotides, usually at least 25 nucleotides, and not more than about 5 kb, usually not more than about 1 kb, preferably not more than about 100 nucleotides. They will typically be approximately 30 nucleotides. They will normally be chosen to bind to different sequences of the analyte. The first binding sequences may be selected based on a variety of considerations. Depending upon the nature of the analyte, one may be interested in a consensus sequence, a sequence associated with polymorphisms, a particular phenotype or genotype, a particular strain, or the like.

By appropriate selection of the first binding sequences of the amplifier and capture probes they may be used to identify a specific nucleic acid molecule that includes a particular gene or other sequence that is present as part of different nucleic acid molecules. In order to discriminate the nucleic acid molecule of interest from other molecules that also contain the given sequence, one of the probes is made complementary to the given sequence while the other is made complementary to another sequence of the molecule which other sequence is unique to that molecule (i.e., is not present in the other molecules that contain the given sequence).

The second binding sequences of the capture probe and amplifier probe are selected to be complementary, respectively, to the oligonucleotide branch to the polystyrene surface and to a segment of the multimer and so as to not be encountered by endogenous sequences in the sample/analyte. The second binding sequence may be contiguous to the first binding sequence or be spaced therefrom by an intermediate noncomplementary sequence. The probes may include other noncomplementary sequences if desired. These noncomplementary sequences must not hinder the binding of the binding sequences or cause nonspecific binding to occur.

The capture probe and amplifier probe may be prepared by oligonucleotide synthesis procedures or by cloning, preferably the former.

It will be appreciated that the binding sequences need not have perfect complementarity to provide homoduplexes. In many situations, heteroduplexes will suffice where fewer than about 10% of the bases are mismatches, ignoring loops of five or more nucleotides. Accordingly, as used herein the term "complementary" intends a degree of complementarity sufficient to provide a stable duplex structure.

The labeled oligonucleotide will include a sequence complementary to the repeated oligonucleotide units of the multimer. The labeled oligonucleotide will include one or more molecules ("labels"), which directly or indirectly provide for a detectable signal. The labels may be bound to individual members of the complementary sequence or may be present as a terminal member or terminal tail having a plurality of labels. Various means for providing labels bound to the sequence have been reported in the literature. See, for example, Leary et al., *Proc Natl Acad Sci USA* (1983) 80:4045; Renz and Kurz, *Nucl Acids Res* (1984) 12:3435; Richardson and Gumport, *Nucl Acids Res* (1983) 11:6167; Smith et al., *Nucl Acids Res* (1985) 13:2399; Meinkoth and Wahl, *Anal Biochem* (1984) 138:267. The labels may be bound either covalently or non-covalently to the complementary sequence. Labels which may be employed include radionuclides, fluorescers, chemiluminescers, dyes, enzymes, enzyme substrates, enzyme cofactors, enzyme inhibitors, enzyme subunits, metal ions, and the like. Illustrative specific labels include fluorescein, rhodamine, Texas red, phycoerythrin, umbelliferone, luminol, NADPH, α-β-galactosidase, horseradish peroxidase, etc.

The ratio of capture probe and amplifier probe to anticipated moles of analyte will each be at least stoichiometric and preferably in excess. This ratio is preferably at least about 1.5:1, and more preferably at least 2:1. It will normally be in the range of 2:1 to 10,000:1. Concentrations of each of the probes will generally range from about $10^{-10}$ to $10^{-6}$M, with sample nucleic acid concentrations varying from $10^{-21}$ to $10^{-12}$M. The hybridization steps of the assay will generally take from about 10 minutes to 2 hours, frequently being completed in about 1 hour. Hybridization can be carried out at a mildly elevated temperature, generally in the range from about 20° C. to 80° C., more usually from about 35° C. to 70° C., particularly 65° C.

The hybridization reactions are usually done in an aqueous medium, particularly a buffered aqueous medium, which may include various additives. Additives which may be employed include low concentrations of detergent (0.1 to 1%), salts, e.g., sodium citrate (0.017 to 0.17M), Ficoll, polyvinylpyrrolidine, carrier nucleic acids, carrier proteins, etc. Nonaqueous solvents may be added to the aqueous medium, such as dimethylformamide, dimethylsulfoxide, alcohols, and formamide. These other solvents will be present in amounts ranging from 2 to 50%.

The stringency of the hybridization medium may be controlled by temperature, salt concentration, solvent system, and the like. Thus, depending upon the length and nature of the sequence of interest, the stringency will be varied.

Depending upon the nature of the label, various techniques can be employed for detecting the presence of the label. For fluorescers, a large number of different fluorometers are available. For chemiluminescers, luminometers or films are available. With enzymes, a fluorescent, chemiluminescent, or colored product can be provided and determined fluorometrically, luminometrically, spectrophotometrically or visually. The various labels which have been employed in immunoassays and the techniques applicable to immunoassays can be employed with the subject assays.

The following examples further illustrate the invention. These examples are not intended to limit the invention in any manner.

EXAMPLE 1

White Microlite 1 Removawell strips (polystyrene microtiter plates, 96 wells/plate) were purchased from Dynatech Inc.

Pre-Wash

Each well was filled with 200 µl 6N HCl and incubated at room temperature for 15–20 min. The plates were then washed 4 times with 1×PBS and the wells aspirated to remove liquid. The wells were then filled with 200 µl 6N NaOH and incubated at room temperature for 15–20 min. The plates were again washed 4 times with 1×PBS and the wells aspirated to remove liquid.

Poly(phe-lys) Coating

Poly(phe-lys) was purchased from Sigma Chemicals, Inc. This polypeptide has a 1:1 molar ratio of phe:lys and an average m.w. of 47,900 gm/mole. It has an average length of 309 amino acids and contains 155 amines/mole. 30 mL of a 1 mg/mL solution of the polypeptide was mixed with 2M NaCl/0.5×PBS to a final concentration of 0.1 mg/mL (pH 6.0). 100 µL of this solution was added to each well. The plate was wrapped in plastic to prevent drying and incubated at 30° C. overnight. The plate was then washed 4 times with 1×PBS and the wells aspirated to remove liquid.

First Stripping

200 µL of 0.2N NaOH containing 0.5 wt % SDS was added to the polypeptide-coated wells. The plate was wrapped in plastic and incubated at 65° C. for 1 hr. The plate was then washed 4 times with 1×PBS and the wells aspirated to remove liquid.

Oligonucleotide Activation 50 mg aliquots of disuccinimidyl suberate (DSS) were each dissolved in 500 µl dimethylformamide (DMF). 26 $OD_{260}$ units of the above-described 21-mer oligonucleotide (designated XT1*) in 1×PBS was added to each aliquot of DSS-DMF. The mixture was vortexed and incubated at room temperature for 30 min. Two NAP25 columns (1, 50 µl aliquot per 26 $OD_{260}$) were equilibrated with 1×PBS, the DSS-DMF-oligonucleotide mix was diluted with 2 mL 1×PBS, and the diluted mix was loaded quickly onto the columns. The columns were allowed to drain and the eluent was discarded. Activated oligonucleotide was eluted from each column with 3.5 ml of 1×PBS, collecting the entire column into 100 ml 1×PBS.

Coupling of Activated Oligonucleotide to Poly(phe-lys)-Coated Plates

50 µL of the activated oligonucleotide-containing eluent was added to each well and the wells were incubated at room temperature for 120 min. The plate was then washed 4 times with 1×PBS and the wells aspirated to remove liquid.

Final Stripping

200 µL of 0.2N NaOH containing 0.5 wt % SDS was added to each well. The plate was wrapped in plastic and incubated at 65° C. for 60 min. The plate was then washed 4 times with 1×PBS and the wells aspirated to remove liquid. The stripped plate was stored with desiccant beads at 2°–8° C.

EXAMPLE 2

Pre-Wash

Microlite 1 Removawell polystyrene microtiter plates were prewashed as in Example 1, except that 1N HCl and 1N NaOH were used.

Polypeptide Coating

The wells were coated as in Example 1. The first stripping step was eliminated.

Oligonucleotide Activation

XT1* oligonucleotide was activated as in Example 1, except that: the molar ratio of DSS to XT1* was 400:1 instead of 1000:1; the buffer and pH used during activation was sodium phosphate at pH 7.8; the buffer and pH used to quench activation was sodium phosphate at pH 6.5; and the temperature and buffer used to purify the activated oligonucleotide was sodium phosphate at pH 6.5, 4° C.

Coupling Activated Oligonucleotide to Coated Wells

Coupling was carried out as in Example 1, except that the buffer was sodium phosphate, pH 7.8 and the incubation was overnight.

Stripping

The wells were stripped with 0.2N NaOH/0.5 wt % SDS as in Example 1.

EXAMPLE 3

The immobilization procedures of Examples 1 and 2 were repeated using varying amounts of activated oligonucleotides used in the coupling step. The amounts of oligonucleotide bound to the well surface was determined in each of these experiments. FIG. 1 is a graph showing the results of these experiments. As indicated, the procedure of Example 2 results in about 10 times more oligonucleotide bound to the surface at a given amount of activated oligonucleotide added to the well.

EXAMPLE 4

This example illustrates the use of the invention in an HCV RNA assay and relates the sensitivity of the assay to the amount of probe immobilized on the plate.

Synthesis of Multimer Used in Assay

A "15×3" amplified solution phase nucleic acid sandwich hybridization assay was employed in this example. The "15×3" designation derives from the fact that the format employs a comb-type multimer having a first segment that hybridizes to the amplifier probe and fifteen iterations of a second segment that hybridizes to three labeled oligonucleotide probes.

The 15×3 comb-type branched oligonucleotide having 15 branch sites and sidechain extensions having three labeled oligonucleotide binding sites was synthesized as follows.

All chemical syntheses of oligonucleotides were performed on an automatic DNA synthesizer (Applied Biosystems, Inc., (ABI) model 380 B). Phosphoramidite chemistry of the beta cyanoethyl type was used including 5'-phosphorylation which employed Phostel™ reagent (ABN). Standard ABI protocols were used except as indicated. Where it is indicated that a multiple of a cycle was used (e.g., 1.2 cycle), the multiple of the standard amount of amidite recommended by ABI was employed in the specified cycle. Appended hereto are the programs for carrying out cycles 1.2 and 6.4 as run on the Applied Biosystems Model 380 B DNA Synthesizer.

A comb body of the following structure was first prepared:

$$3'T_{18}(TTX')_{15}GTTTGTGG\text{-}5'$$
$$|$$
$$(RGTCAGTp\text{-}5')_{15}$$

wherein X' is a branching monomer, and R is a periodate cleavable linker.

The portion of the comb body through the 15 (TTX') repeats is first synthesized using 33.8 mg aminopropyl-derivitized thymidine controlled pore glass (CPG) (2000 Å, 7.4 micromoles thymidine per gram support) with a 1.2 cycle protocol. The branching site nucleotide was of the formula:

where R² represents

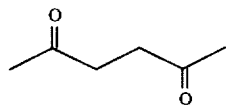

For synthesis of the comb body (not including sidechains), the concentration of beta cyanoethylphosphoramidite monomers was 0.1M for A, C, G and T, 0.15M for the branching site monomer E, and 0.2M for Phostel™ reagent. Detritylation was done with 3% trichloroacetic acid in methylene chloride using stepped flowthrough for the duration of the deprotection. At the conclusion the 5' DMT was replaced with an acetyl group.

Cleavable linker R and six base sidechain extensions of the formula 3'-RGTCAGTp were synthesized at each branching monomer site as follows. The base protecting group removal (R² in the formula above) was performed manually while retaining the CPG support in the same column used for synthesizing the comb body. In the case of R²=levulinyl, a solution of 0.5M hydrazine hydrate in pyridine/glacial acetic acid (1:1 v/v) was introduced and kept in contact with the CPG support for 90 min with renewal of the liquid every 15 min, followed by extensive washing with pyridine/glacial acetic acid (1:1 v/v) and then by acetonitrile. After the deprotection the cleavable linker R and six base sidechain extensions were added using a 6.4 cycle.

In these syntheses the concentration of phosphoramidites was 0.1M (except 0.2M R and Phostel™ reagent; R was 2-(4-(4-(2-Dimethoxytrityloxy)ethyl)-phenoxy 2,3-di(benzoyloxy)-butaneoxy)phenyl)ethyl-2-cyanoethyl-N,N-diisopropylphosphoramidite).

Detritylation is effected with a solution of 3% trichloroacetic acid in methylene chloride using continuous flowthrough, followed by a rinse solution of toluene/chloromethane (1:1 v/v). Branched polynucleotide chains were removed from the solid supports automatically in the 380B using the cycle "CE NH₃." The ammonium hydroxide solution was collected in 4 ml screw-capped Wheaton vials and heated at 60° C. for 12 hr to remove all base-protecting groups. After cooling to room temperature the solvent was removed in a Speed-Vac evaporator and the residue dissolved in 100 μl water.

3' backbone extensions (segment A), sidechain extensions and ligation template/linkers of the following structures were also made using the automatic synthesizer:

3' Backbone extension  3'-TCCGTATCCTGGGCACAGAGGTGCp-5' (SEQ ID NO:2)

Sidechain extension  3'-GATGCG(TTCATGCTGTTGGTGTAG)₃-5' (SEQ ID NO:3)

Ligation template for linking 3' backbone extension  3'-AAAAAAAAAAGCACCTp-5' (SEQ ID NO:4)

Ligation template for linking sidechain extension  3'-AAAAAAAAAAGCACCTp-5' (SEQ ID NO:5)

The crude comb body was purified by a standard polyacrylamide gel (7% with 7M urea and 1X TBE running buffer) method.

The 3' backbone extension and the sidechain extensions were ligated to the comb body as follows. The comb body (4 pmole/μl), 3' backbone extension (6.25 pmole/μl), sidechain extension (93.75 pmole/μl), sidechain linking template (93.75 pmole/μl), and backbone linking template (5 pmole/μl) were combined in 1 mm ATP/ 5 mM DTT/ 50 mM Tris-HCl₁, pH 8.0/ 10 mM MgCl₂/2 mM spermidine, with 0.5 units/μl T4 polynucleotide kinase. The mixture was incubated at 37° C. for 2 hr, then heated in a water bath to 95° C., and then slowly cooled to below 35° C. over a 1 hr period. 2 mM ATP, 10 mM DTT, 14% polyethylene glycol, and 0.21 units/μl T4 ligase were added, and the mixture incubated for 16–24 hr at 23° C. The DNA was precipitated in NaCl/ethanol, resuspended in water, and subjected to a second ligation as follows. The mixture was adjusted to 1 mm ATP, 5 mm DTT, 14% polyethylene glycol, 50 mM Tris-HCl, pH 7.5, 10 mM MgCl₂, 2 mM spermidine, 0.5 units/μl T4 polynucleotide kinase, and 0.21 units/μl T4 ligase were added, and the mixture incubated at 23° C. for 16–24 hr. Ligation products were then purified by polyacrylamide gel electrophoresis.

Label and Capture Probes Used

The amplifier (label) and capture probe HCV-specific segments used in this assay were as follows:

Probes complementary to nucleotide sequences in the HCV E1 gene of Group I viral isolates (see FIG. 2A):

| Probe Type | Probe Number | Complement of Nucleotide Numbers |
|---|---|---|
| Label | 27A (SEQ ID NO: 6) | 879–911 |
| Label | 28A (SEQ ID NO: 7) | 912–944 |
| Capture | 29A (SEQ ID NO: 8) | 945–977 |
| Label | 30A (SEQ ID NO: 9) | 978–1010 |
| Label | 31A (SEQ ID NO: 10) | 1011–1043 |
| Label | 32A (SEQ ID NO: 11) | 1044–1076 |
| Label | 33A (SEQ ID NO: 12) | 1077–1109 |
| Capture | 34A (SEQ ID NO: 13) | 1110–1142 |
| Label | 35A (SEQ ID NO: 14) | 1143–1175 |
| Label | 36A (SEQ ID NO: 15) | 1176–1208 |
| Label | 37A (SEQ ID NO: 16) | 1209–1241 |
| Label | 38A (SEQ ID NO: 17) | 1242–1274 |
| Capture | 39A (SEQ ID NO: 18) | 1275–1307 |
| Label | 40A (SEQ ID NO: 19) | 1308–1340 |
| Label | 41A (SEQ ID NO: 20) | 1341–1373 |
| Label | 42A (SEQ ID NO: 21) | 1274–1406 |
| Label | 43A (SEQ ID NO: 22) | 1407–1439 |
| Capture | 44A (SEQ ID NO: 23) | 1440–1472 |
| Label | 45A (SEQ ID NO: 24) | 1473–1505 |

Probes complementary to nucleotide sequences in the HCV E1 gene of Group II viral isolates (see FIG. 2B):

| Probe Type | Probe Number | Complement of Nucleotide Numbers |
|---|---|---|
| Label | 27A (SEQ ID NO: 25) | 879–911 |
| Label | 28A (SEQ ID NO: 26) | 912–944 |
| Capture | 29A (SEQ ID NO: 27) | 945–977 |
| Label | 30A (SEQ ID NO: 28) | 978–1010 |
| Label | 31A (SEQ ID NO: 29) | 1011–1043 |
| Label | 32A (SEQ ID NO: 30) | 1044–1076 |
| Label | 33A (SEQ ID NO: 31) | 1077–1109 |
| Capture | 34A (SEQ ID NO: 32) | 1110–1142 |
| Label | 35A (SEQ ID NO: 33) | 1143–1175 |
| Label | 36A (SEQ ID NO: 34) | 1176–1208 |
| Label | 37A (SEQ ID NO: 35) | 1209–1241 |
| Label | 38A (SEQ ID NO: 36) | 1242–1274 |
| Capture | 39A (SEQ ID NO: 37) | 1275–1307 |
| Label | 40A (SEQ ID NO: 38) | 1308–1340 |
| Label | 41A (SEQ ID NO: 70) | 1341–1373 |
| Label | 42A (SEQ ID NO: 39) | 1274–1406 |
| Label | 43A (SEQ ID NO: 40) | 1407–1439 |
| Capture | 44A (SEQ ID NO: 41) | 1440–1472 |
| Label | 45A (SEQ ID NO: 42) | 1473–1505 |

Probes complementary to nucleotide sequences in the C gene and the 5'-untranslated region (see FIG. 3):

| Probe Type | Probe Number |
|---|---|
| Capture | HCV.33.1 (SEQ ID NO: 43) |
| Label | HCV.33.2 (SEQ ID NO: 44) |
| Label | HCV.33.3 (SEQ ID NO: 45) |
| Label | HCV.33.4 (SEQ ID NO: 46) |
| Capture | HCV.33.5 (SEQ ID NO: 47) |
| Label | HCV.33.6 (SEQ ID NO: 48) |
| Label | HCV.33.7 (SEQ ID NO: 49) |
| Label | HCV.33.8 (SEQ ID NO: 50) |
| Capture | HCV.33.9 (SEQ ID NO: 51) |
| Label | HCV.33.10 (SEQ ID NO: 52) |
| Label | HCV.33.11 (SEQ ID NO: 53) |
| Label | HCV.33.12 (SEQ ID NO: 54) |
| Capture | HCV.33.13 (SEQ ID NO: 55) |
| Label | HCV.33.14 (SEQ ID NO: 56) |
| Label | HCV.33.15 (SEQ ID NO: 57) |
| Label | HCV.33.16A (SEQ ID NO: 58) |
| Label | HCV.33.16B (SEQ ID NO: 59) |
| Capture | HCV.33.17 (SEQ ID NO: 60) |
| Label | HCV.33.18 (SEQ ID NO: 61) |
| Label | HCV.33.19 (SEQ ID NO: 62) |
| Label | HCV.33.20 (SEQ ID NO: 63) |
| Capture | HCV.33.21 (SEQ ID NO: 64) |
| Label | HCV.33.22 (SEQ ID NO: 65) |
| Label | HCV.33.23 (SEQ ID NO: 66) |
| Label | HCV.33.24 (SEQ ID NO: 67) |
| Capture | HCV.33.25 (SEQ ID NO: 68) |
| Label | HCV.33.26 (SEQ ID NO: 69) |

In the above sets, each capture probe contained, in addition to the sequences complementary to the HCV sequences, a downstream sequence complementary to XT1*.

Assay Format

Extraction buffer of the following range was prepared.
Extraction Buffer Recipe—100 ml Recipe for 100 ml:
  5.3 ml 1M Tris-HCl, pH 8
  4.24 ml 0.25M EDTA
  13 ml 10% SDS
  160 µl 10 mg/ml sssDNA
  26.5 ml 20×SSC
  7 ml Deionized Formamide
  93 mg Proteinase K The Tris, EDTA, SDS, sonicated salmon sperm DNA and SSC were added to 25 ml deionized water and the volume was adjusted to 93 ml with deionized water. The solution was mixed gently and the pH was adjusted to 7.5. The proteinase K was added to the solution and mixed until dissolved. The solution was incubated at 37° C. in a water bath for 3 hr. The solution was cooled to room temperature and the formamide was added.

Hybridization buffer of the following recipe was made by mixing the contents with resting to form a solution.

Hybridization Buffer Recipe—1L Recipe for 1 Liter:
  5 gr Blocking Reagent
  10 ml 10% SDS
  200 ml 20x SSC
  DI water to 1 liter Twenty-five µl each of the capture and label probes were added to 3,000 µl of PK buffer (12 mg proteinase K dissolved in 6 ml of extraction buffer). Fifty µl of this mixture was added to the wells of a microtiter plate prepared as in Example 2, followed by the addition of 50 µl of the sample suspected of containing HCV nucleic acid. The plate is covered with Mylar and incubated at 65° C. for 16 hr. The plate was then cooled, the Mylar removed, the wells aspirated, washed with 1x wash buffer (0.1% SDS/0.015M NaCl/0.0015M sodium citrate) and aspirated again.

A solution of the multimer (25 fmol/50 µl) in hybridization buffer was prepared and 50 µl was added to each well. The plate was covered with Mylar, agitated for 30 seconds and incubated at 55° C. for 30 minutes. The plate was then cooled, the Mylar removed, washed with 1x wash buffer, and aspirated.

Figure 4:
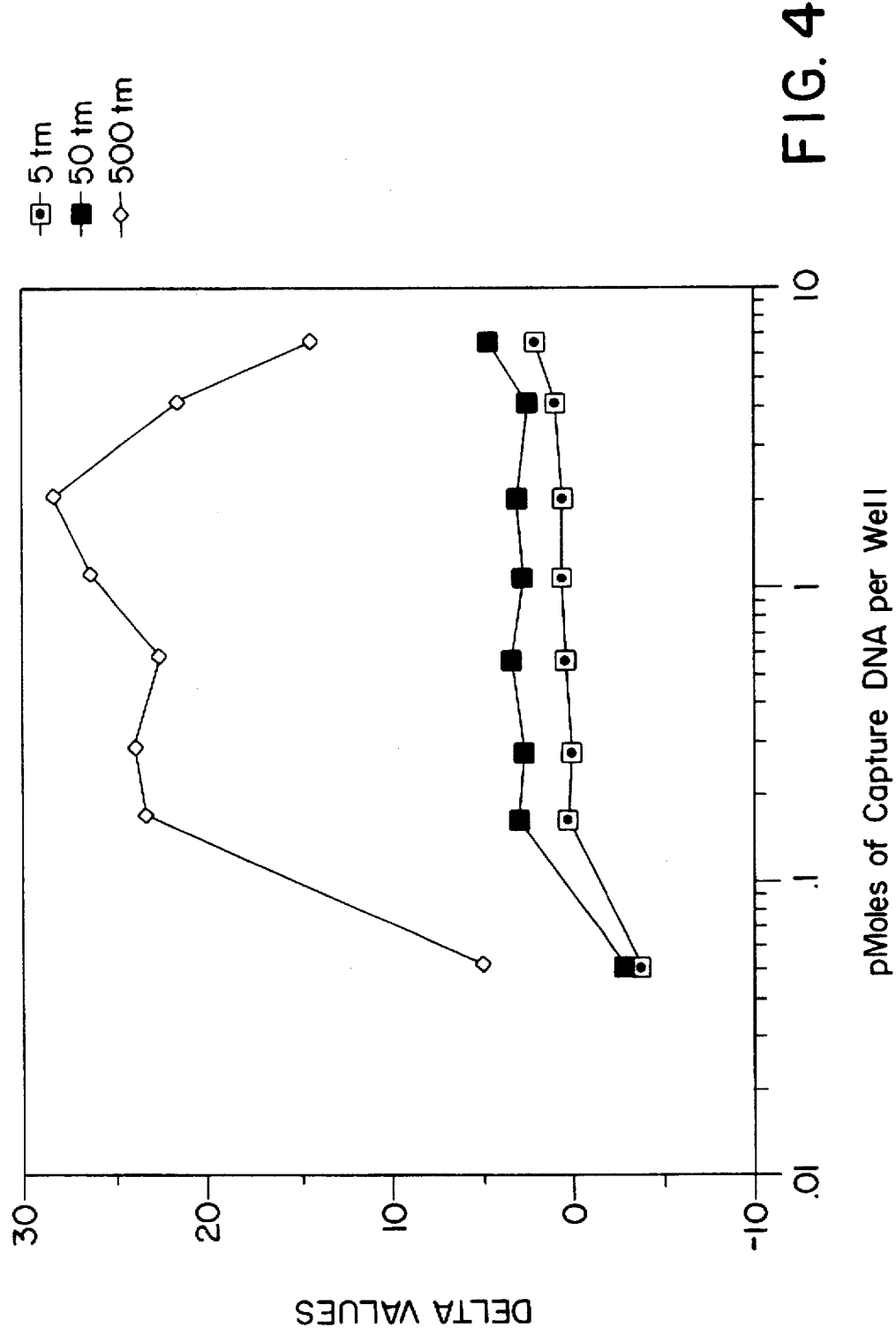
FIG. 4 is a graph of the results of the tests described in Example 4.

The assay was carried out on specimens containing, respectively, HCV RNA at 5, 50, and 500 tipomoles (tm, 1 tipomole=602 molecules, or $10^{-21}$ mole) using microtiter plates prepared as in Example 2 with varying amounts of immobilized (capture) DNA per well. Sensitivity was characterized as a delta value=(mean−2 std dev)−(zero+2 std dev). FIG. 4 reports the results of these assays. As indicated, optimum sensitivity for this assay occurs at 0.1 to 1.1 pmoles of immobilized DNA per well.

EXAMPLE 5

Assays for HBV DNA were carried out using the format described in Example 4 above and microtiter plates coated as in Example 2 above but using various polypeptide coatings. In these assays, poly(phe-lys), casein, Boehringer-Mannheim "blocking reagent" (#1096176 Boehringer-Mannheim Catalog), poly(ala-glu) and poly(glu-lys) coated plates exhibited similar performance in the assay.

Modifications of the above-described modes for carrying out the invention that are obvious to those of skill in biochemistry, nucleic acid hybridization assays, and related fields are intended to be within the scope of the following claims.

We claim:

1. An article of manufacture for use in a solution phase nucleic acid sandwich hybridization assay comprising a polystyrene surface having a polypeptide adsorbed thereon and a nucleic acid probe covalently bonded to the polypeptide via a base-stable bifunctional crosslinking agent.

2. The article of manufacture of claim 1 wherein the article is a well of a microtiter plate.

3. The article of manufacture of claim 1 wherein the article is a bead.

4. The article of manufacture of claim 2 wherein there are about 0.1 to 10 pmoles of the probe on the surface.

5. The article of manufacture of claim 4 wherein there are about 0.4 to 0.7 pmoles of the probe in the well surface.

6. An article of manufacture for use in a solution phase nucleic acid sandwich hybridization assay comprising a polystyrene surface having a polypeptide adsorbed thereon and a nucleic acid probe covalently bonded to the polypeptide via a base-stable bifunctional crosslinking agent, wherein the polypeptide is poly(phe-lys), the crosslinking agent is disuccinimidyl suberate, and the nucleic acid probe is 5'-XCACCACTTTCTCCAAAGAAG-3' (SEQ ID NO: 1) where X represents the $N^4$-(6-aminocaproyl-2-aminoethyl) derivative of cytidine.

* * * * *

SEQUENCE LISTING ( 1 ) GENERAL INFORMATION:

( i i i ) NUMBER OF SEQUENCES: 70

( 2 ) INFORMATION FOR SEQ ID NO:1:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i x ) FEATURE:
        ( D ) OTHER INFORMATION: At nucleotide 1, N is N4-(6-
        aminocaproyl- 2-aminoethyl) cytosine.

( x i ) SEQUENCE DESCRIPTION: SEQ ID NO:1:

NCACCACTTT CTCCAAAGAA G                                            21

( 2 ) INFORMATION FOR SEQ ID NO:2:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2:

CGTGGAGACA CGGGTCCTAT GCCT                                24

( 2 ) INFORMATION FOR SEQ ID NO:3:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:3:

GATGTGGTTG TCGTACTTGC GTAG                                 24

( 2 ) INFORMATION FOR SEQ ID NO:4:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:4:

TCCACGAAAA AAAAAA                                                        16

( 2 ) INFORMATION FOR SEQ ID NO:5:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:5:

CAGTCACTAC GC                                                               12

( 2 ) INFORMATION FOR SEQ ID NO:6:

( i ) SEQUENCE CHARACTERISTICS:

(A) LENGTH: 33 base pairs
(B) TYPE: nucleic acid
(C) STRANDEDNESS: single
(D) TOPOLOGY: linear (x i) SEQUENCE DESCRIPTION: SEQ ID NO:6:

YGAAGCGGGC ACAGTCARRC AAGARAGCAG GGC    33

(2) INFORMATION FOR SEQ ID NO:7:

(i) SEQUENCE CHARACTERISTICS:
(A) LENGTH: 33 base pairs
(B) TYPE: nucleic acid
(C) STRANDEDNESS: single
(D) TOPOLOGY: linear (x i) SEQUENCE DESCRIPTION: SEQ ID NO:7:

RTARAGCCCY GWGGAGTTGC GCACTTGGTR GGC    33

(2) INFORMATION FOR SEQ ID NO:8:

(i) SEQUENCE CHARACTERISTICS:
(A) LENGTH: 33 base pairs
(B) TYPE: nucleic acid
(C) STRANDEDNESS: single
(D) TOPOLOGY: linear (x i) SEQUENCE DESCRIPTION: SEQ ID NO:8:

RATACTCGAG TTAGGGCAAT CATTGGTGAC RTG    33

(2) INFORMATION FOR SEQ ID NO:9:

(i) SEQUENCE CHARACTERISTICS:
(A) LENGTH: 33 base pairs
(B) TYPE: nucleic acid
(C) STRANDEDNESS: single
(D) TOPOLOGY: linear (x i) SEQUENCE DESCRIPTION: SEQ ID NO:9:

AGYRTGCAGG ATGGYATCRK BCGYCTCGTA CAC    33

(2) INFORMATION FOR SEQ ID NO:10:

(i) SEQUENCE CHARACTERISTICS:
(A) LENGTH: 33 base pairs
(B) TYPE: nucleic acid
(C) STRANDEDNESS: single
(D) TOPOLOGY: linear (x i) SEQUENCE DESCRIPTION: SEQ ID NO:10:

GTTRCCCTCR CGAACGCAAG GGACRCACCC CGG    33

(2) INFORMATION FOR SEQ ID NO:11:

(i) SEQUENCE CHARACTERISTICS:
(A) LENGTH: 33 base pairs
(B) TYPE: nucleic acid
(C) STRANDEDNESS: single
(D) TOPOLOGY: linear (x i) SEQUENCE DESCRIPTION: SEQ ID NO:11:

CGTRGGGGTY AYCGCCACCC AACACCTCGA GRC    33

(2) INFORMATION FOR SEQ ID NO:12:

(i) SEQUENCE CHARACTERISTICS:
(A) LENGTH: 33 base pairs
(B) TYPE: nucleic acid (C) STRANDEDNESS: single
(D) TOPOLOGY: linear (xi) SEQUENCE DESCRIPTION: SEQ ID NO:12:

CGTYGYGGGG AGTTTGCCRT CCCTGGTGGC YAC　　　　　　　　　　　　33

(2) INFORMATION FOR SEQ ID NO:13:

(i) SEQUENCE CHARACTERISTICS:
(A) LENGTH: 33 base pairs
(B) TYPE: nucleic acid
(C) STRANDEDNESS: single
(D) TOPOLOGY: linear (xi) SEQUENCE DESCRIPTION: SEQ ID NO:13:

CCCGACAAGC AGATCGATGT GACGTCGAAG CTG　　　　　　　　　　　　33

(2) INFORMATION FOR SEQ ID NO:14:

(i) SEQUENCE CHARACTERISTICS:
(A) LENGTH: 33 base pairs
(B) TYPE: nucleic acid
(C) STRANDEDNESS: single
(D) TOPOLOGY: linear (xi) SEQUENCE DESCRIPTION: SEQ ID NO:14:

CCCCACGTAG ARGGCCGARC AGAGRGTGGC GCY　　　　　　　　　　　　33

(2) INFORMATION FOR SEQ ID NO:15:

(i) SEQUENCE CHARACTERISTICS:
(A) LENGTH: 33 base pairs
(B) TYPE: nucleic acid
(C) STRANDEDNESS: single
(D) TOPOLOGY: linear (xi) SEQUENCE DESCRIPTION: SEQ ID NO:15:

YTGRCCGACA AGAAAGACAG ACCCGCAYAR GTC　　　　　　　　　　　　33

(2) INFORMATION FOR SEQ ID NO:16:

(i) SEQUENCE CHARACTERISTICS:
(A) LENGTH: 33 base pairs
(B) TYPE: nucleic acid
(C) STRANDEDNESS: single
(D) TOPOLOGY: linear (xi) SEQUENCE DESCRIPTION: SEQ ID NO:16:

CGTCCAGTGG YGCCTGGGAG AGAAGGTGAA CAG　　　　　　　　　　　　33

(2) INFORMATION FOR SEQ ID NO:17:

(i) SEQUENCE CHARACTERISTICS:
(A) LENGTH: 33 base pairs
(B) TYPE: nucleic acid
(C) STRANDEDNESS: single
(D) TOPOLOGY: linear (xi) SEQUENCE DESCRIPTION: SEQ ID NO:17:

GCCGGGATAG ATRGARCAAT TGCARYCTTG CGT　　　　　　　　　　　　33

(2) INFORMATION FOR SEQ ID NO:18:

(i) SEQUENCE CHARACTERISTICS:
(A) LENGTH: 33 base pairs
(B) TYPE: nucleic acid
(C) STRANDEDNESS: single
(D) TOPOLOGY: linear ( x i ) SEQUENCE DESCRIPTION: SEQ ID NO:18:

CATATCCCAT GCCATGCGGT GACCCGTTAY ATG        33

( 2 ) INFORMATION FOR SEQ ID NO:19:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:19:

YACCAAYGCC GTCGTAGGGG ACCARTTCAT CAT        33

( 2 ) INFORMATION FOR SEQ ID NO:20:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:20:

GATGGCTTGT GGGATCCGGA GYASCTGAGC YAY        33

( 2 ) INFORMATION FOR SEQ ID NO:21:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:21:

GACTCCCCAG TGRGCWCCAG CGATCATRTC CAW        33

( 2 ) INFORMATION FOR SEQ ID NO:22:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:22:

CCCCACCATG GAGAAATACG CTATGCCCGC YAG        33

( 2 ) INFORMATION FOR SEQ ID NO:23:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:23:

TAGYAGCAGY ACTACYARGA CCTTCGCCCA GTT        33

( 2 ) INFORMATION FOR SEQ ID NO:24:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:24:

```
GSTGACGTGR  GTKTCYGCGT  CRACGCCGGC  RAA                                    33
```

( 2 ) INFORMATION FOR SEQ ID NO:25:

( i ) SEQUENCE CHARACTERISTICS:
    ( A ) LENGTH: 33 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:25:

```
GGAAGYTGGG  ATGGTYARRC  ARGASAGCAR  AGC                                    33
```

( 2 ) INFORMATION FOR SEQ ID NO:26:

( i ) SEQUENCE CHARACTERISTICS:
    ( A ) LENGTH: 33 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:26:

```
GTAYAYYCCG  GACRCGTTGC  GCACTTCRTA  AGC                                    33
```

( 2 ) INFORMATION FOR SEQ ID NO:27:

( i ) SEQUENCE CHARACTERISTICS:
    ( A ) LENGTH: 33 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:27:

```
AATRCTTGMG  TTGGAGCART  CGTTYGTGAC  ATG                                    33
```

( 2 ) INFORMATION FOR SEQ ID NO:28:

( i ) SEQUENCE CHARACTERISTICS:
    ( A ) LENGTH: 33 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:28:

```
RGYRTGCATG  ATCAYGTCCG  YYGCCTCATA  CAC                                    33
```

( 2 ) INFORMATION FOR SEQ ID NO:29:

( i ) SEQUENCE CHARACTERISTICS:
    ( A ) LENGTH: 33 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:29:

```
RTTGTYYTCC  CGRACGCARG  GCACGCACCC  RGG                                    33
```

( 2 ) INFORMATION FOR SEQ ID NO:30:

( i ) SEQUENCE CHARACTERISTICS:
    ( A ) LENGTH: 33 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:30:

```
CGTGGGRGTS  AGCGCYACCC  AGCARCGGGA  GSW                                    33
```

( 2 ) INFORMATION FOR SEQ ID NO:31:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:31:

YGTRGTGGGG AYGCTGKHRT TCCTGGCCGC VAR        33

( 2 ) INFORMATION FOR SEQ ID NO:32:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:32:

CCCRACGAGC AARTCGACRT GRCGTCGTAW TGT        33

( 2 ) INFORMATION FOR SEQ ID NO:33:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:33:

YCCCACGTAC ATAGCSGAMS AGARRGYAGC CGY        33

( 2 ) INFORMATION FOR SEQ ID NO:34:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:34:

CTGGGAGAYR AGRAAAACAG ATCCGCARAG RTC        33

( 2 ) INFORMATION FOR SEQ ID NO:35:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:35:

YGTCTCRTGC CGGCGAGSBG AGAAGGTGAA YAG        33

( 2 ) INFORMATION FOR SEQ ID NO:36:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:36:

GCCGGGATAG AKKGAGCART TGCAKTCCTG YAC        33

( 2 ) INFORMATION FOR SEQ ID NO:37:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:37:

CATATCCCAA GCCATRCGRT GGCCTGAYAC GTG      33

( 2 ) INFORMATION FOR SEQ ID NO:38:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:38:

CACTARGGCT GYYGTRGGYG ACCAGTTCAT CAT      33

( 2 ) INFORMATION FOR SEQ ID NO:39:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:39:

GACTCCCCAG TGRGCCCCCG CCACCATRTC CAT      33

( 2 ) INFORMATION FOR SEQ ID NO:40:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:40:

SCCCACCATG GAWWAGTAGG CAAGGCCCGC YAG      33

( 2 ) INFORMATION FOR SEQ ID NO:41:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:41:

GAGTAGCATC ACAATCAADA CCTTAGCCCA GTT      33

( 2 ) INFORMATION FOR SEQ ID NO:42:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:42:

YGWCRYGYRG GTRTKCCCGT CAACGCCGGC AAA      33

( 2 ) INFORMATION FOR SEQ ID NO:43:

( i ) SEQUENCE CHARACTERISTICS:
    ( A ) LENGTH: 33 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:43:

TCCTCACAGG GGAGTGATTC ATGGTGGAGT GTC    33

( 2 ) INFORMATION FOR SEQ ID NO:44:

( i ) SEQUENCE CHARACTERISTICS:
    ( A ) LENGTH: 33 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:44:

ATGGCTAGAC GCTTTCTGCG TGAAGACAGT AGT    33

( 2 ) INFORMATION FOR SEQ ID NO:45:

( i ) SEQUENCE CHARACTERISTICS:
    ( A ) LENGTH: 33 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:45:

GCCTGGAGGC TGCACGRCAC TCATACTAAC GCC    33

( 2 ) INFORMATION FOR SEQ ID NO:46:

( i ) SEQUENCE CHARACTERISTICS:
    ( A ) LENGTH: 33 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:46:

CGCAGACCAC TATGGCTCTY CCGGGAGGGG GGG    33

( 2 ) INFORMATION FOR SEQ ID NO:47:

( i ) SEQUENCE CHARACTERISTICS:
    ( A ) LENGTH: 33 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:47:

TCRTCCYGGC AATTCCGGTG TACTCACCGG TTC    33

( 2 ) INFORMATION FOR SEQ ID NO:48:

( i ) SEQUENCE CHARACTERISTICS:
    ( A ) LENGTH: 33 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:48:

GCATTGAGCG GGTTDATCCA AGAAAGGACC CGG    33

( 2 ) INFORMATION FOR SEQ ID NO:49:

( i ) SEQUENCE CHARACTERISTICS:
    ( A ) LENGTH: 33 base pairs ( B ) TYPE: nucleic acid
( C ) STRANDEDNESS: single
( D ) TOPOLOGY: linear ( x i ) SEQUENCE DESCRIPTION: SEQ ID NO:49:

AGCAGTCTYG CGGGGGCACG CCCAARTCTC CAG      33

( 2 ) INFORMATION FOR SEQ ID NO:50:

( i ) SEQUENCE CHARACTERISTICS:
( A ) LENGTH: 33 base pairs
( B ) TYPE: nucleic acid
( C ) STRANDEDNESS: single
( D ) TOPOLOGY: linear ( x i ) SEQUENCE DESCRIPTION: SEQ ID NO:50:

ACAAGGCCTT TCGCGACCCA ACACTACTCG GCT      33

( 2 ) INFORMATION FOR SEQ ID NO:51:

( i ) SEQUENCE CHARACTERISTICS:
( A ) LENGTH: 33 base pairs
( B ) TYPE: nucleic acid
( C ) STRANDEDNESS: single
( D ) TOPOLOGY: linear ( x i ) SEQUENCE DESCRIPTION: SEQ ID NO:51:

GGGGCACTCG CAAGCACCCT ATCAGGCAGT ACC      33

( 2 ) INFORMATION FOR SEQ ID NO:52:

( i ) SEQUENCE CHARACTERISTICS:
( A ) LENGTH: 33 base pairs
( B ) TYPE: nucleic acid
( C ) STRANDEDNESS: single
( D ) TOPOLOGY: linear ( x i ) SEQUENCE DESCRIPTION: SEQ ID NO:52:

CCCTCCAGAG CATCTGGCAC GTRGTACTCG TGY      33

( 2 ) INFORMATION FOR SEQ ID NO:53:

( i ) SEQUENCE CHARACTERISTICS:
( A ) LENGTH: 33 base pairs
( B ) TYPE: nucleic acid
( C ) STRANDEDNESS: single
( D ) TOPOLOGY: linear ( x i ) SEQUENCE DESCRIPTION: SEQ ID NO:53:

TWAGGRTTTG GRGTTTYTTY TTKGTTTGCA TTG      33

( 2 ) INFORMATION FOR SEQ ID NO:54:

( i ) SEQUENCE CHARACTERISTICS:
( A ) LENGTH: 33 base pairs
( B ) TYPE: nucleic acid
( C ) STRANDEDNESS: single
( D ) TOPOLOGY: linear ( x i ) SEQUENCE DESCRIPTION: SEQ ID NO:54:

TGGTTGGCRG CGGGTGTCCT GCARTTCAAG GGC      33

( 2 ) INFORMATION FOR SEQ ID NO:55:

( i ) SEQUENCE CHARACTERISTICS:
( A ) LENGTH: 33 base pairs
( B ) TYPE: nucleic acid
( C ) STRANDEDNESS: single -continued ( D ) TOPOLOGY: linear ( x i ) SEQUENCE DESCRIPTION: SEQ ID NO:55:

CCRCCRCCRG TCTAGCARCC ACCTCAAATG RAC     33

( 2 ) INFORMATION FOR SEQ ID NO:56:

( i ) SEQUENCE CHARACTERISTICS:
    ( A ) LENGTH: 33 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:56:

RCGCACACCC AAYCTRGGGC CCCTGCGCGG CAA     33

( 2 ) INFORMATION FOR SEQ ID NO:57:

( i ) SEQUENCE CHARACTERISTICS:
    ( A ) LENGTH: 33 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:57:

AGGTTGCGAC CGCTCGGAAG TCTTYCTRGT CGC     33

( 2 ) INFORMATION FOR SEQ ID NO:58:

( i ) SEQUENCE CHARACTERISTICS:
    ( A ) LENGTH: 33 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:58:

RCGHRCCTTG GGGATAGGCT GACGTCWACC TCG     33

( 2 ) INFORMATION FOR SEQ ID NO:59:

( i ) SEQUENCE CHARACTERISTICS:
    ( A ) LENGTH: 33 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:59:

RCGHRCCTTG GGGATAGGTT GTCGCCWTCC ACG     33

( 2 ) INFORMATION FOR SEQ ID NO:60:

( i ) SEQUENCE CHARACTERISTICS:
    ( A ) LENGTH: 33 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:60:

YCCRGGCTGR GCCCAGRYCC TRCCCTCGGR YYG     33

( 2 ) INFORMATION FOR SEQ ID NO:61:

( i ) SEQUENCE CHARACTERISTICS:
    ( A ) LENGTH: 33 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:61:

BSHRCCCTCR TTRCCRTAGA GGGGCCADGG RTA                33

( 2 ) INFORMATION FOR SEQ ID NO:62:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:62:

GCCRCGGGGW GACAGGAGCC ATCCYGCCCA CCC                33

( 2 ) INFORMATION FOR SEQ ID NO:63:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:63:

CCGGGGGTCY GTGGGGCCCC AYCTAGGCCG RGA                33

( 2 ) INFORMATION FOR SEQ ID NO:64:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:64:

ATCGATGACC TTACCCAART TRCGCGACCT RCG                33

( 2 ) INFORMATION FOR SEQ ID NO:65:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:65:

CCCCATGAGR TCGGCGAAGC CGCAYGTRAG GGT                33

( 2 ) INFORMATION FOR SEQ ID NO:66:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:66:

GCCYCCWARR GGGGCGCCGA CGAGCGGWAT RTA                33

( 2 ) INFORMATION FOR SEQ ID NO:67:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:67:

```
AACCCGGACR  CCRTGYGCCA  RGGCCCTGGC  AGC                              3 3
```

( 2 ) INFORMATION FOR SEQ ID NO:68:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:68:

```
RTTCCCTGTT  GCATAGTTCA  CGCCGTCYTC  CAG                              3 3
```

( 2 ) INFORMATION FOR SEQ ID NO:69:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:69:

```
CARRAGGAAG  AKAGAGAAAG  AGCAACCRGG  MAR                              3 3
```

( 2 ) INFORMATION FOR SEQ ID NO:70:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:70:

```
GACRGCTTGT  GGGATCCGGA  GTAACTGCGA  YAC                              3 3
```